(12) United States Patent
Shepard

(10) Patent No.: US 6,795,784 B1
(45) Date of Patent: Sep. 21, 2004

(54) DATA INTEGRATION AND REGISTRATION METHOD AND APPARATUS FOR NON-DESTRUCTIVE EVALUATION OF MATERIALS

(75) Inventor: Steven M. Shepard, Southfield, MI (US)

(73) Assignee: Thermal Wave Imaging, Inc., Ferndale, MI (US)

( * ) Notice: Subject to any disclaimer, the term of this patent is extended or adjusted under 35 U.S.C. 154(b) by 0 days.

(21) Appl. No.: 09/623,071
(22) PCT Filed: Feb. 25, 1999
(86) PCT No.: PCT/US99/04206
§ 371 (c)(1),
(2), (4) Date: Jan. 12, 2001
(87) PCT Pub. No.: WO99/44366
PCT Pub. Date: Sep. 2, 1999

Related U.S. Application Data

(60) Provisional application No. 60/075,920, filed on Feb. 25, 1998.

(51) Int. Cl.[7] .................................................. G06K 9/00
(52) U.S. Cl. ......................................................... 702/82
(58) Field of Search ...................... 702/82, 39; 348/125, 348/135; 382/151; 328/4; 386/93; 250/950, 341.8, 259, 330; 219/745; 354/288; 356/237; 376/216; 359/612; 361/683; 364/507; 73/626; 128/661; 474/20

(56) References Cited

U.S. PATENT DOCUMENTS

| | | | | | |
|---|---|---|---|---|---|
| 5,300,746 A | * | 4/1994 | Walters et al. | ............... | 219/745 |
| 5,351,307 A | * | 9/1994 | Prejean-Lefevre | .......... | 382/151 |
| 5,444,241 A | * | 8/1995 | Del Grande et al. | ......... | 250/253 |
| 5,475,613 A | * | 12/1995 | Itoga et al. | .................... | 702/39 |
| 5,541,696 A | * | 7/1996 | Bittner | ........................ | 359/612 |
| 5,703,362 A | * | 12/1997 | Devitt et al. | ................. | 250/330 |
| 5,748,496 A | * | 5/1998 | Takahashi et al. | ........... | 376/216 |
| 5,801,919 A | * | 9/1998 | Griencewic | ................ | 361/683 |
| 6,072,900 A | * | 6/2000 | Chiu et al. | ................... | 382/149 |
| 6,091,847 A | * | 7/2000 | Chiu et al. | ................... | 382/149 |

* cited by examiner

*Primary Examiner*—John Barlow
*Assistant Examiner*—Tung S. Lau
(74) *Attorney, Agent, or Firm*—Honigman, Miller, Schwartz and Cohn LLP

(57) ABSTRACT

A method an apparatus for non-destructive testing and evaluation of part samples includes obtaining a defect image of the sample, displaying the defect image on a display, referencing the defect image, such as through marking or annotation, to highlight locations at which defects or measurements are found, superimposing the defect image onto a live image of the part, and physically marking/annotating the part, tracing the marks from the defect image onto the physical sample, while viewing the live image. Because both the defect image and the live image are viewed through the same camera lens and are therefore subject to the same amount of distortion, the actual sample can be marked exactly according to the marks made in the defect image; there is no need to attempt matching a distorted defect image with the physical sample, as has been done in the prior art. This one-to-one correspondence between the defect image and the live display enables precise marking of the physical sample since the user looks at the distorted live image of the sample, not the physical sample itself, during the marking process. The method is particularly useful for detecting subsurface defects in a sample via thermographic techniques.

21 Claims, 4 Drawing Sheets

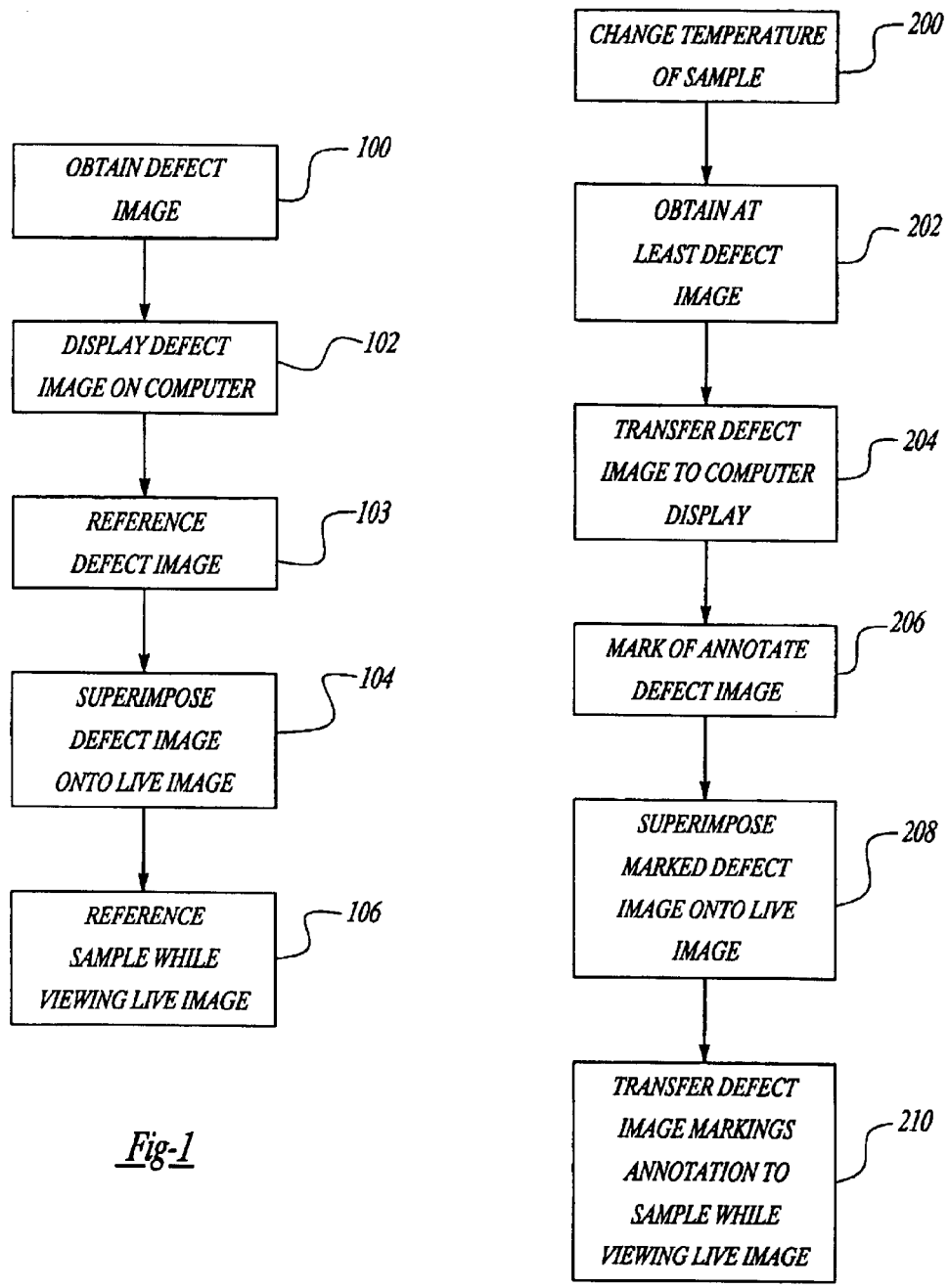

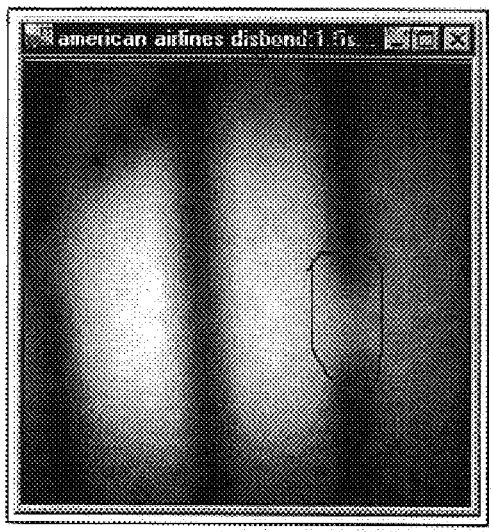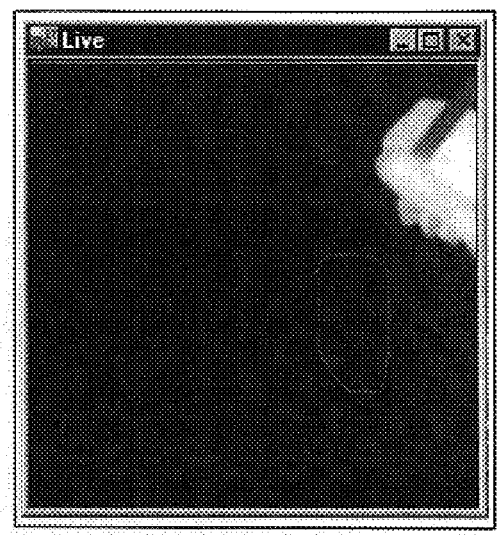
Fig-3E                    Fig-3F

120
DATA INTEGRATION AND REGISTRATION METHOD AND APPARATUS FOR NON-DESTRUCTIVE EVALUATION OF MATERIALS

This application claims the benefit of provisional application No. 60/075,920, filed Feb. 25, 1998.

TECHNICAL FIELD

The present invention is directed to a method and apparatus for non-destructive testing and evaluation of materials, and more particularly to a method and apparatus for identifying and registering defects in a sample by superimposing a defect image over a live image to locate subsurface defects in the sample.

BACKGROUND ART

Various methods of non-destructive testing and evaluation (NDT/E) of parts have been developed to detect subsurface defects in a part sample and to measure the depth of subsurface defects. These methods include step thermography, pulse thermography, and other thermographic techniques. All of these techniques involve deliberately changing the temperature of the sample, and observing the temperature change of the sample via an infrared (IR) camera as it returns to equilibrium temperature. Anomalous temperature changes that appear in the infrared camera image indicate subsurface defects in the sample; subsurface defects tend to impede the normal heat flow in the sample and will appear as anomalies in the image. Further, because the infrared image showing the defect is transient and may last for only a fraction of a second, the image must be captured (usually with a digital computer) and then verified against the actual sample to locate the exact position of the defect.

The actual verification process, usually through a complementary NDT/E process, can be relatively difficult because the infrared defect image of the sample may bear little resemblance to the actual sample. For example, many subsurface defects appear only in the infrared image; to the naked eye, the sample containing the defects often appears perfectly uniform. As a result, a user must attempt to match the infrared image of the subsurface defect with the actual, unblemished sample surface to pinpoint the location of the defect. This is further complicated by the fact that the infrared camera lens often distorts the image, causing straight lines at the periphery of the lens's field of view to appear curved in the image. To locate and mark the positions of subsurface defects with some precision, prior art methods include using regularly spaced registration markers on the sample, calculating complex anamorphic mapping algorithms, or printing a full-size defect image and physically matching or overlaying the full-size image onto the actual sample. Because the sample may not have any distinguishing marks that appear in the defect image, precise registration of the image and the sample's surface can be difficult. In addition, these methods are time-consuming and are not particularly convenient, and at best they can only approximate the subsurface defect location due to the image distortion from the infrared camera lens. Further, measuring the depth of subsurface defects often requires some prior knowledge of the sample's dimensions or properties, such as the thickness of the sample, the depth of a known defect, the material's thermal diffusivity, etc. This information is often not available in practice, making precise depth measurements difficult with known techniques.

Thus, there currently is a need for a NDT/E technique that allows accurate annotation, marking, and thickness measurements of specific locations on a sample, without the problems caused by differences between the image and the actual sample due to image distortion. There is also a need for a NDT/E technique that can conduct depth measurement without requiring prior knowledge of any of the sample's characteristics. If the depth and onset time (relative to the heating event) of a single defect are known, it is then possible to calculate the thermal diffusivity of the material and to use it to determine the depths of other defects from their offset time, according to the well-known relation of $t=d^2/D$, where t is the onset time, d is the depth of the defect, and D is the thermal diffusivity of the sample.

SUMMARY OF THE INVENTION

Accordingly, the present invention is a method and apparatus for conducting NDT/E that simplifies the correspondence between image information obtained during NDT/E and the actual sample. More specifically, the invention involves obtaining a defect image and a live image of the same sample and then superimposing one image on the other. One embodiment of the invention is directed to linking the information regarding surface defects obtained during infrared NDT/E to the actual part being inspected. The invention includes generating a defect image of the sample via infrared imaging or some other means. The defect image may have markers or other indicia locating where subsurface defects are in the sample. The defect image is then superimposed onto a live image of the sample. A user then views the live image of the sample, rather than the sample itself, while transferring the marks from the defect image to the sample. Because both the defect image and the live image are distorted by the infrared camera lens and therefore have a one-to-one correspondence, the distorted image is used as the frame of reference for locating subsurface defects and marking the sample. This ensures that the marks in the defect image are transferred precisely from the defect image onto the sample and also eliminates the need to map the distorted image to the sample in a separate step.

BRIEF DESCRIPTION OF THE DRAWINGS

FIG. 1 is a flowchart illustrating an evaluation and testing method according to the present invention;

FIG. 2 is a flowchart illustrating an example of the inventive method as applied to thermography;

FIGS. 3a through 3f illustrate actual images taken from infrared NDT/E of an aluminum aircraft panel according to the method of the present invention.

DETAILED DESCRIPTION OF THE PREFERRED EMBODIMENT

Figure 3A:
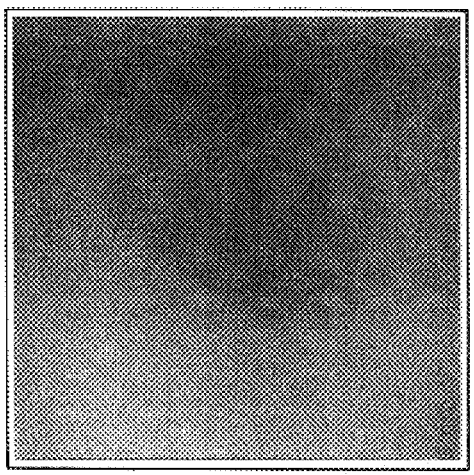

Referring to FIG. 1, one embodiment of the NDT/E method according to the present invention can be broken down into four steps. First, a defect image of the sample is obtained 100, digitized and displayed on a computer 102 using a computer program that has a referencing mechanism, such as drawing tool that allows the user to draw on the defect image using a mouse, touch screen, light pen, or other pointing device. The user can mark defects found in the defect image with the drawing tool 103. The defect image, including any marks made by the user, is then superimposed onto a live image 104, which is also displayed and maintained on the computer display device (the term "live image" as used throughout this description is an image displayed in real time on a computer display device, such as a CRT, such that any markings or movement made by an operator are captured in real time within the "live image" and are immediately displayed by the display device). The live image is preferably produced immediately thereafter and using the same lens and camera that produced the defect image to ensure a one-to-one correspondence between the live image and the defect image; using the same lens ensures that both images will have the same distortion. The user then marks the actual sample, using a marking pencil or similar device, while viewing the live image 106 rather than looking the sample itself. Instead of marking the part, the user may also use a point measuring device to measure characteristics of the sample, such as its thickness, and append the data to the image for annotation or calibration purposes. The defect image and live image can also be simply superimposed one atop the other for referencing purposes, without any user intervention.

As noted above, the defect image is subject to any lens distortion that may be present. In the prior art, inaccuracies in marking occurred because the user was attempting to map the distorted defect image onto a corresponding physical sample part, whether it was through markers on the sample or through overlaying a full-size image on the actual sample. In the invention, however, the user watches the live image of the sample rather than the sample itself when referencing the sample. Because the live image and the defect image in the present invention are both distorted via the same camera lens, the defect image and the live image align perfectly with each other. Further, the user will look at the live image of the marking or measurement instrument, and not the actual marking/measurement instrument itself, in real time while referencing the sample, making it possible to trace the marks from the defect image onto the sample precisely and distortion-free. In short, the distorted defect image and the distorted live image both have exactly the same, albeit distorted, frame of reference. Thus, any marks or measurements taken while viewing the live image will correspond exactly to the marked locations in the defect image superimposed on the live image.

Figure 3B:
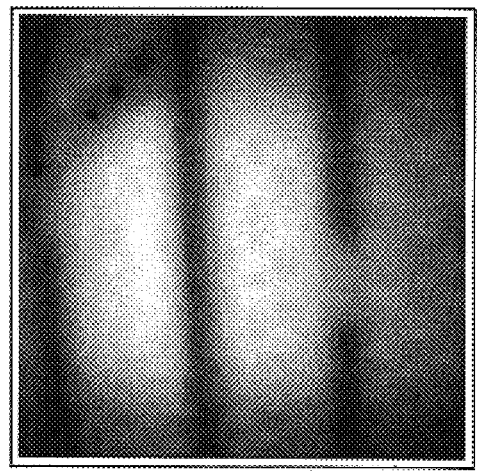
Figure 3C:
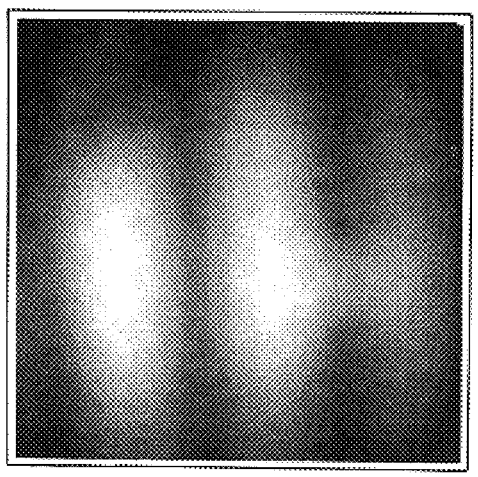
Figure 3D:
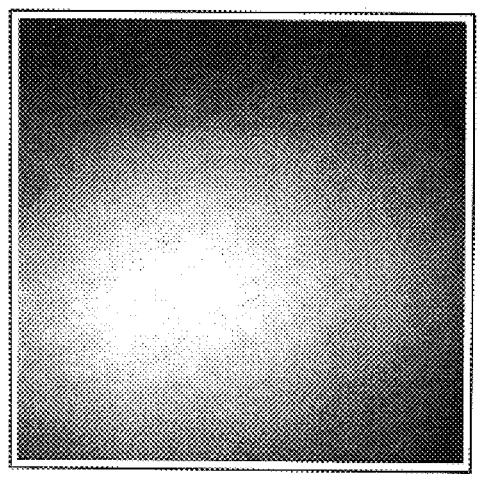

Referring now to FIGS. 2 and 3*a* through 3*f*, the method of the present invention will now be described with respect to thermography. Note that the invention is not limited to such an application and can be used in any application where accurate mapping between an image of a sample and the sample itself is needed. The first step involves changing the sample's temperature 200 by heating or cooling the temperature through any known method. For example, heat can be applied to the sample via a flashlamp or a continuous lighting source. Defect images of the sample are then taken 202 with an infrared camera as the sample's temperature returns to equilibrium. The infrared camera preferably obtains multiple defect images from the same sample after the sample's temperature is changed, taking images at selected time intervals as the sample returns to equilibrium temperature. FIGS. 3*a* through 3*d* illustrate a time sequence of infrared images of an aluminum aircraft pane adhesively bonded to an aluminum structural frame, illustrating the transient nature of infrared NDT/E. FIG. 3*a* was taken just before heating, FIG. 3*b* taken 1.33 seconds after heating, FIG. 3*c* taken 10.67 seconds after heating, and FIG. 3*d* taken 39.34 seconds after heating. As can be seen in the figures, the aircraft panel does not exhibit any subsurface structure before heating (FIG. 3*a*), while just after heating, the frame can be seen in the defect image, along with a disbonded area where corrosion has occurred, in the right half of the image (FIG. 3*b*). The frame and disbanded area are less distinct after 10.67 seconds (FIG. 3*c*) and disappear completely after 39.34 seconds (FIG. 3*d*). For non-destructive evaluation, the image obtained shown in FIG. 3*b* provides the most useful information because it is the clearest image.

Once the desired defect image is selected, it is digitized and transferred to the computer 204 for display on a computer monitor. The defect image is preferably displayed using a program with a "draw" mode so that the user can place marks on the defect image using a mouse, touch screen, or other pointing device. The area where the defects occur is then "marked" on the screen by the user 206. An example of such a display is shown in FIG. 3*e*, where the image from FIG. 3*b* is taken as the defect image. As can be seen in FIG. 3*e*, the area where the plate defect appears has been circled by the user, using the "draw" mode in the computer program generating the defect image, to highlight the area at which the subsurface defect is located.

Once the defect image is marked 206, it is superimposed onto a digitized live image 208, which is also displayed on the computer monitor. As explained above, because both the defect image and the live image are obtained using the same infrared camera lens and because the camera is not moved after the defect image is obtained, both the defect image and the live image exhibit the same amount of lens distortion and have a one-to-one correspondence with each other; the defect image and live image do not have any distortion with respect to each other. Once the defect image is superimposed on the live image, the user can transfer the reference marks from the defect image to the sample 210 exactly and distortion-free. As shown in FIG. 3*f*, the user does this by viewing his hand (or the marking instrument) on the sample via the live image, not by directly watching the physical sample. Because of the one-to-one correspondence between the defect image and the live image, and because the user views the live image while referencing the actual sample, the marks are made on the actual sample precisely correspond to the location of the defect. Alternatively, or in addition to the marking, the user may also contact the sample with a point measuring probe, such as an ultrasonic thickness gauge or thermocouple, to measure the local properties of the sample. Because the probe will appear in the live image, the user can mark the position of the probe on the defect image and then read the probe measurement through a serial data connection. The information can be appended to the image for annotation or calibration purposes.

Many different apparatus configurations can be used to carry out the method of the present invention. For example, although the above method has been described using a digital computer for receiving image data from the infrared camera, many infrared cameras have onboard displays and dedicated microcontrollers. Thus, most if not all of the steps explained above can be integrated into the camera itself. The user can perform the outlining/marking operation using cursor keys already resident on the camera. Further, the marking/annotation steps can be conducted using image processing/machine vision methods rather than manually by the user. Also, all of the above steps can be completely automated if, for example, a 3-D map of the sample is stored in the computer. In such a case, the computer itself could conduct the superimposing, referencing, and correlating based on the information in the 3-D map, without user intervention.

Figure 4:
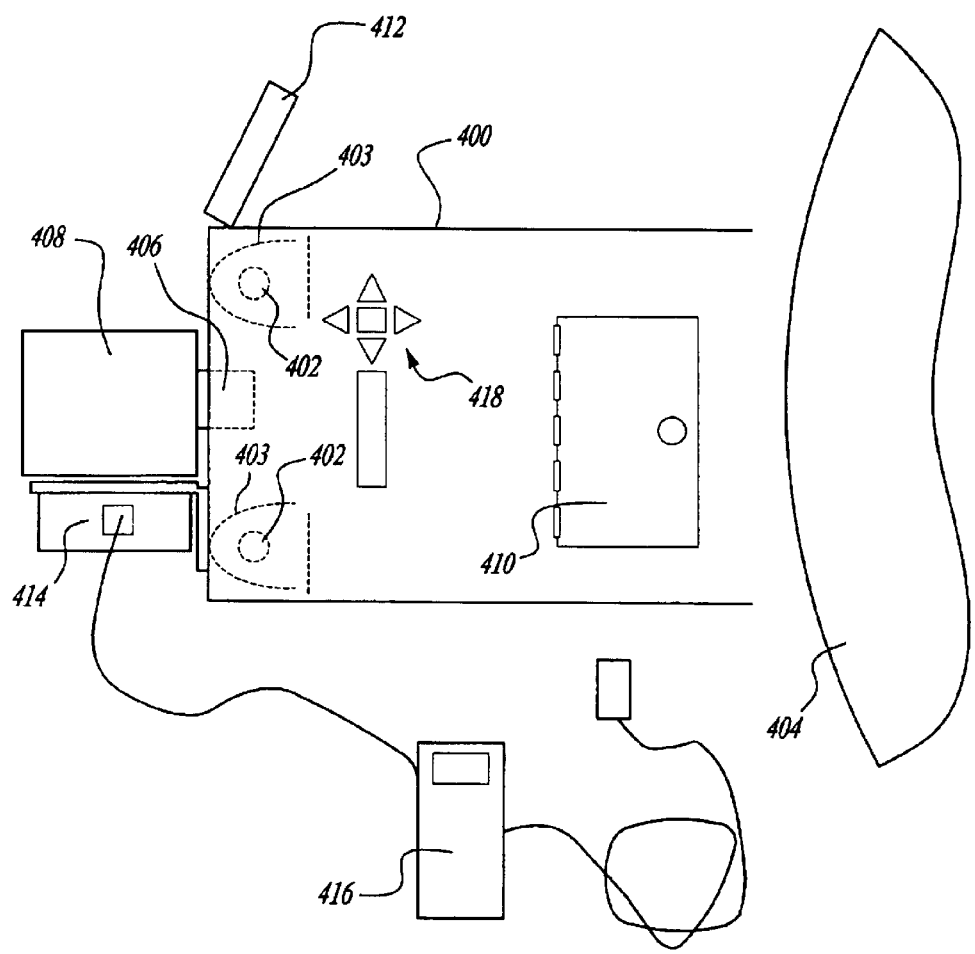
FIG. 4 is a representative diagram of an apparatus that can be used to annotate, calibrate, and/or evaluate a sample according to the method of the present invention.

FIG. 4 illustrates one apparatus that can be used to carry out the inventive method with respect to thermography. The apparatus includes a reflective hood 400 that focuses light from heating lamps 402 onto a sample 404. The heating lamps 402 can be flashlamps (e.g. xenon lamps) or continuous lamps (e.g. halogen lamps). Regardless of the type of lamp used, reflectors 403 or some other means should be used to distribute light uniformly over the sample 404 surface at the opinion of the hood 400 so that the sample heats evenly. The front end of the hood 400 is open and is placed on or near the sample 404. The back portion of the hood 400 is designed to accommodate a lens 406 of an infrared camera 408. The hood 400 also preferably has an access door 410 to allow the user to reach inside the hood 400 and mark the sample, if desired.

The apparatus shown in FIG. 4 also includes a display 412 for displaying the defect image and the live image generated by the infrared camera 408. The apparatus also includes a microcontroller or personal computer 414, which may be located in the infrared camera 408 itself, attached to the thermography apparatus in some other way, or located remotely and accessed via 2-way serial or parallel data communication. A measuring instrument 416, such as an ultrasonic thickness gauge, can also be provided to conduct thickness measurements or other measurements. Lastly, a user interface 418, such as an operator keypad or touch screen, is provided on the apparatus to allow marking of the defect image and manipulation of the images on the display 412.

In summary, because the invention uses a distorted live image and a distorted defect image to locate subsurface defects, the one-to-one correspondence between the two distorted images creates a new frame of reference from which to pinpoint the defect locations, greatly increasing the accuracy and speed at which subsurface defects can be located and marked. The invention also allows complementary NDT/E methods to be used in conjunction with the defect image so that the defect image can be annotated or can be calibrated so thickness measurements can be obtained directly from the image, without requiring prior information from a reference sample or any other source. Further, the invention can be used with any infrared NDT/E method, independently of how the method changes the sample's temperature, generates the defect image, or processes the data.

It should be understood that various alternatives to the embodiments of the invention described herein may be employed in practicing the invention. It is intended that the following claims define the scope of the invention and that the method and apparatus within the scope of these claims and their equivalents be covered thereby.

I claim:

1. A method for non-destructive evaluation of a sample, comprising the steps of:
   obtaining a defect image of said sample by collecting infrared light irradiated from said sample,
   displaying a real time image of said sample on a display device, wherein the defect image and the real time image of said sample have a one-to-one correspondence with each other; and
   superimposing one of the defect image and the real time displayed image onto the other of the defect image and the real time displayed image.

2. The method of claim 1, further comprising the steps of:
   locating a defect in the sample by way of the defect image;
   referencing the sample while viewing said superimposed real time image and the referenced defect image on said display device.

3. The method of claim 2, wherein the step of referencing the sample includes the step of marking the sample according to the referenced defect image.

4. The method of claim 2, wherein the step of referencing the sample includes the step of measuring a characteristic of the sample at a selected location.

5. A method for non-destructive evaluation of a sample, comprising the steps of:
   obtaining a defect image of said sample,
   displaying a real time image of said sample on display device, wherein the defect image and the real time image have a one-to-one correspondence with each other;
   displaying the defect image on a digital display device;
   superimposing the defect image onto the display of the real time image; and
   referencing the sample while viewing, on the display device, the superimposed real time and defect images wherein the defect image is an infrared image, and wherein the defect image and the live image are obtained from an infrared camera.

6. The method of claim 5, further comprising the steps of:
   changing the temperature of the sample; and
   obtaining at least one defect image over a time period of temperature change of said sample.

7. The method of claim 6, wherein the changing step includes directing a heating pulse onto the sample such that the heat is distributed generally evenly over the sample.

8. The method of claim 6, wherein the changing step includes directing continuous heat onto the sample that the heat is distributed generally evenly over the sample.

9. The method of claim 5, wherein the reference step includes the steps of:
   measuring a characteristic of the sample at a selected location; and
   annotating the defect image with data obtained from the measuring step.

10. The method of claim 5, wherein the referencing step includes the steps of:
    measuring a characteristic of the sample at a selected location; and
    annotating the defect image with data obtained from the measuring step.

11. The method of claim 5, wherein the obtaining, displaying, superimposing and referencing steps are automated and conducted in a computer.

12. An apparatus for non-destructive testing/evaluation of a sample, comprising:
    a camera that captures a defect image and generates a real time image of the sample;
    a processor coupled with the camera to digitize the defect image and the real time image;
    a display for displaying the digitized defect image and the real time image, wherein the processor and the display include means for referencing the defect image and superimposing one of the defect image and the real time image onto the other of the defect image and the real time image wherein the camera is an infrared camera, and wherein the apparatus further comprises:
    a hood having a reflective interior and an opening for the camera at a back portion and an open end at the front portion, wherein the sample is disposed in the front portion of the hood; and
    at least one heating lamp disposed inside the hood to heat the sample.

13. The apparatus of claim 12, wherein the processor and the display are constructed as part of the camera.

14. The apparatus of claim 12, wherein the hood has a door to allow physical access to the sample by the user.

15. A computer readable storage device for non-destructive evaluation of a sample, comprising the steps of:

obtaining a defect image and a real time image of the sample, the defect image and the real time image having a one-to-one correspondence with each other;

displaying the defect image on a digital display;

superimposing the defect image onto the real time image on the display; and referencing the sample while viewing the real time image and the defect image on the display wherein the defect image is an infrared image, and wherein the defect image and the real time image are obtained from an infrared camera.

16. The computer readable storage device of claim 15, further comprising the step of:

changing the temperature of the sample; and obtaining at least one defect image over a period of time where the sample temperature is changing.

17. The computer readable storage device of claim 16, wherein the changing step includes directing a heating pulse onto the sample such that the heat is distributed evenly over the sample.

18. The computer readable storage device of claim 16, wherein the changing step includes directing continuous heat onto the sample such that the heat is distributed evenly over the sample.

19. The computer readable storage device of claim 15, wherein the referencing step includes the step of:

measuring a characteristic of the sample at a selected location; and annotating the defect image with data obtained from the measuring step.

20. The computer readable storage device of claim 15, wherein the referencing step includes the steps of:

measuring a characteristic of the sample at a selected location; and annotating the defect image with data obtained from the measuring step.

21. The computer readable storage device of claim 15, wherein the obtaining, displaying, superimposing and referencing steps are automated and conducted in a computer.

\* \* \* \* \*

UNITED STATES PATENT AND TRADEMARK OFFICE
CERTIFICATE OF CORRECTION

PATENT NO. : 6,795,784 B1  Page 1 of 1
DATED : September 21, 2004
INVENTOR(S) : Shepard It is certified that error appears in the above-identified patent and that said Letters Patent is hereby corrected as shown below:

Column 6,
Line 31, change "onto the sample that the" to -- onto the sample such that the --.

Column 7,
Line 19, change "further comprising the step of:" to -- further comprising the steps of: --

Signed and Sealed this

Twelfth Day of April, 2005

JON W. DUDAS
*Director of the United States Patent and Trademark Office*